(12) United States Patent
Raz et al.

(10) Patent No.: US 11,484,369 B2
(45) Date of Patent: Nov. 1, 2022

(54) IDENTIFYING INSTANCES OF CARDIOVERSION WHILE BUILDING A POSITION MAP

(71) Applicant: Biosense Webster (Israel) Ltd., Yokneam (IL)

(72) Inventors: Shaul Haim Raz, Shimshit (IL); Ofer Klemm, Koranit (IL); Shmuel Auerbach, Kerem Maharal (IL); Moran Morady, Beit Nehemia (IL); Tsafrir Ozer, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 211 days.

(21) Appl. No.: 17/082,120

(22) Filed: Oct. 28, 2020

(65) Prior Publication Data

US 2022/0125521 A1    Apr. 28, 2022

(51) Int. Cl.
*A61B 5/06* (2006.01)
*A61B 34/20* (2016.01)
*A61B 5/00* (2006.01)

(52) U.S. Cl.
CPC ............. *A61B 34/20* (2016.02); *A61B 5/061* (2013.01); *A61B 5/6847* (2013.01); *A61B 2034/2051* (2016.02)

(58) Field of Classification Search
CPC ....... A61B 34/20; A61B 5/061; A61B 5/6847; A61B 2034/2051
See application file for complete search history.

(56) References Cited

U.S. PATENT DOCUMENTS

| 5,391,199 A | 2/1995 | Ben-Haim |
|---|---|---|
| 5,443,489 A | 8/1995 | Ben-Haim |
| 5,558,091 A | 9/1996 | Acker et al. |
| 6,177,792 B1 | 1/2001 | Govari |

(Continued)

FOREIGN PATENT DOCUMENTS

| EP | 3409188 A1 | 12/2018 |
|---|---|---|
| EP | 3473177 A1 | 4/2019 |

OTHER PUBLICATIONS

European Search Report for corresponding European patent application No. 21204960.5, dated Apr. 4, 2022.

*Primary Examiner* — Rochelle D Turchen
(74) *Attorney, Agent, or Firm* — Notaro, Michalos & Zaccaria P.C.

(57) ABSTRACT

A method includes computing a position of an intrabody probe, which includes one or more electrodes and an electromagnetic sensor, within a heart of a subject, based on an induced signal received from the electromagnetic sensor, ascertaining a set of properties of signals passed between the electrodes and multiple reference electrodes located at respective reference positions, based on the set of properties, deriving an estimated position of the probe from a position map that maps multiple sets of properties to respective estimated positions, in response to a distance between the computed position and the estimated position being greater than a predefined threshold, ascertaining whether an electrocardiographic signal from the subject is saturated, and in response to the electrocardiographic signal not being saturated, updating the position map so as to map the set of properties to the computed position. Other embodiments are also described.

9 Claims, 4 Drawing Sheets

(56) References Cited

U.S. PATENT DOCUMENTS

| | | | |
|---|---|---|---|
| 6,690,963 B2 | 2/2004 | Ben-Haim et al. | |
| 6,788,967 B2 | 9/2004 | Ben-Haim | |
| 7,536,218 B2 | 5/2009 | Govari et al. | |
| 9,788,756 B2 | 10/2017 | Demmer | |
| 10,323,922 B2 | 6/2019 | Zeng et al. | |
| 2008/0009758 A1* | 1/2008 | Voth | A61B 5/318 600/523 |
| 2011/0054559 A1* | 3/2011 | Rosenberg | A61N 1/368 607/28 |
| 2015/0057507 A1* | 2/2015 | Koyrakh | A61B 5/7246 600/301 |
| 2019/0053737 A1 | 2/2019 | Carter et al. | |
| 2019/0200886 A1* | 7/2019 | Welsh | A61B 5/25 |
| 2020/0138334 A1* | 5/2020 | Hill | A61B 5/6852 |
| 2020/0196908 A1 | 6/2020 | Ben-Haim et al. | |
| 2021/0145301 A1* | 5/2021 | Ravuna | A61B 5/366 |
| 2022/0202338 A1* | 6/2022 | Zhu | A61B 5/333 |

* cited by examiner

IDENTIFYING INSTANCES OF CARDIOVERSION WHILE BUILDING A POSITION MAP

FIELD OF THE INVENTION

The present invention is related to the tracking of probes during intracardiac procedures.

BACKGROUND

U.S. Pat. No. 7,536,218 to Govari et al., whose disclosure is incorporated herein by reference, describes a position sensing system including a probe adapted to be introduced into a body cavity of a subject. The probe includes a magnetic field transducer and at least one probe electrode. A control unit is configured to measure position coordinates of the probe using the magnetic field transducer. The control unit also measures an impedance between the at least one probe electrodes and one or more points on a body surface of the subject. Using the measured position coordinates, the control unit calibrates the measured impedance.

SUMMARY OF THE INVENTION

There is provided, in accordance with some embodiments of the present invention, a system including a memory, configured to store a position map that maps multiple sets of properties to respective estimated positions, and a processor. The processor is configured to compute a position of an intrabody probe, which includes one or more electrodes and an electromagnetic sensor, within a heart of a subject, based on an induced signal received from the electromagnetic sensor. The processor is further configured to ascertain a set of properties of signals passed between the electrodes and multiple reference electrodes located at respective reference positions. The processor is further configured to derive an estimated position of the probe from the position map, based on the set of properties. The processor is further configured to ascertain whether an electrocardiographic signal from the subject is saturated, in response to a distance between the computed position and the estimated position being greater than a predefined threshold. The processor is further configured to update the position map, in the memory, so as to map the set of properties to the computed position, in response to the electrocardiographic signal not being saturated.

In some embodiments, the predefined threshold is between 8 and 15 mm.

In some embodiments, the predefined threshold is a first predefined threshold, and the processor is configured to update the position map in response to the distance not exceeding a second predefined threshold.

In some embodiments, the processor is configured to ascertain whether the electrocardiographic signal from the subject is saturated in response to the distance not exceeding the second predefined threshold.

In some embodiments, the second predefined threshold is greater than 15 mm.

In some embodiments, the second predefined threshold is between 15 and 30 mm.

In some embodiments, the processor is further configured to: compute another position of the probe and ascertain another set of properties, and in response to the electrocardiographic signal being saturated, refrain from updating the position map so as to map the other set of properties to the other computed position.

In some embodiments, the processor is further configured to, in response to the electrocardiographic signal being saturated, refrain from updating the position map for a predefined duration.

In some embodiments, the predefined duration is between 4 and 5 s.

There is further provided, in accordance with some embodiments of the present invention, a method including computing a position of an intrabody probe, which includes one or more electrodes and an electromagnetic sensor, within a heart of a subject, based on an induced signal received from the electromagnetic sensor. The method further includes ascertaining a set of properties of signals passed between the electrodes and multiple reference electrodes located at respective reference positions. The method further includes, based on the set of properties, deriving an estimated position of the probe from a position map that maps multiple sets of properties to respective estimated positions. The method further includes, in response to a distance between the computed position and the estimated position being greater than a predefined threshold, ascertaining whether an electrocardiographic signal from the subject is saturated. The method further includes, in response to the electrocardiographic signal not being saturated, updating the position map so as to map the set of properties to the computed position.

There is further provided, in accordance with some embodiments of the present invention, a computer software product including a tangible non-transitory computer-readable medium in which program instructions are stored, which instructions, when read by a processor, cause the processor to compute a position of an intrabody probe, which includes one or more electrodes and an electromagnetic sensor, within a heart of a subject, based on an induced signal received from the electromagnetic sensor. The instructions further cause the processor to ascertain a set of properties of signals passed between the electrodes and multiple reference electrodes located at respective reference positions. The instructions further cause the processor to derive an estimated position of the probe from a position map that maps multiple sets of properties to respective estimated positions, based on the set of properties. The instructions further cause the processor to ascertain whether an electrocardiographic signal from the subject is saturated, in response to a distance between the computed position and the estimated position being greater than a predefined threshold. The instructions further cause the processor to update the position map so as to map the set of properties to the computed position, in response to the electrocardiographic signal not being saturated.

The present invention will be more fully understood from the following detailed description of embodiments thereof, taken together with the drawings, in which:

DETAILED DESCRIPTION OF EMBODIMENTS

Overview

U.S. Pat. No. 7,536,218 to Govari et al., cited above in the Background, describes a hybrid tracking system for tracking the position of an intrabody probe. In this system, a probe is provided with an electromagnetic sensor and one or more position-tracking electrodes. While the probe is moved within a body cavity of a subject, signals are induced in the electromagnetic sensor by an external magnetic field, and a processor computes the position of the probe based on the induced signals. In addition, position-tracking signals, whose properties vary with the position of the probe, are passed between the position-tracking electrodes and one or more reference electrodes on the body surface of the subject. The processor builds a position map, which maps the properties of the position-tracking signals to the position of the probe as computed from the induced signals. Subsequently, another probe, which does not include an electromagnetic sensor but includes position-tracking electrodes, may be tracked using the position-tracking electrodes and the position map.

A challenge, when building the position map as described above, is that any cardioversion procedure performed on the subject may alter the properties of the position-tracking signals, such that the position-tracking signals do not accurately indicate the position of the probe. Hence, if the building of the position map continues during a cardioversion procedure, the accuracy of the map is compromised. Given that the cardioverter used for cardioversion is typically not connected to the processor, the processor does not know when a cardioversion is performed.

To address this challenge, embodiments of the present invention use the position map to compute an estimated position of the probe, based on the position-tracking signals. If the estimated position deviates from the "true" position (as computed from the induced signal) by more than a threshold distance, the processor checks whether an electrocardiographic (ECG) signal from the subject is saturated. If the signal is saturated—indicating that a cardioversion is likely in progress—the processor refrains from updating the position map, typically until a predefined amount of time has passed.

Typically, a second, higher threshold distance is also defined. If the estimated position deviates from the true position by more than the second threshold distance, the processor may refrain from updating the position map, even without checking the ECG signal.

System Description

Figure 1:
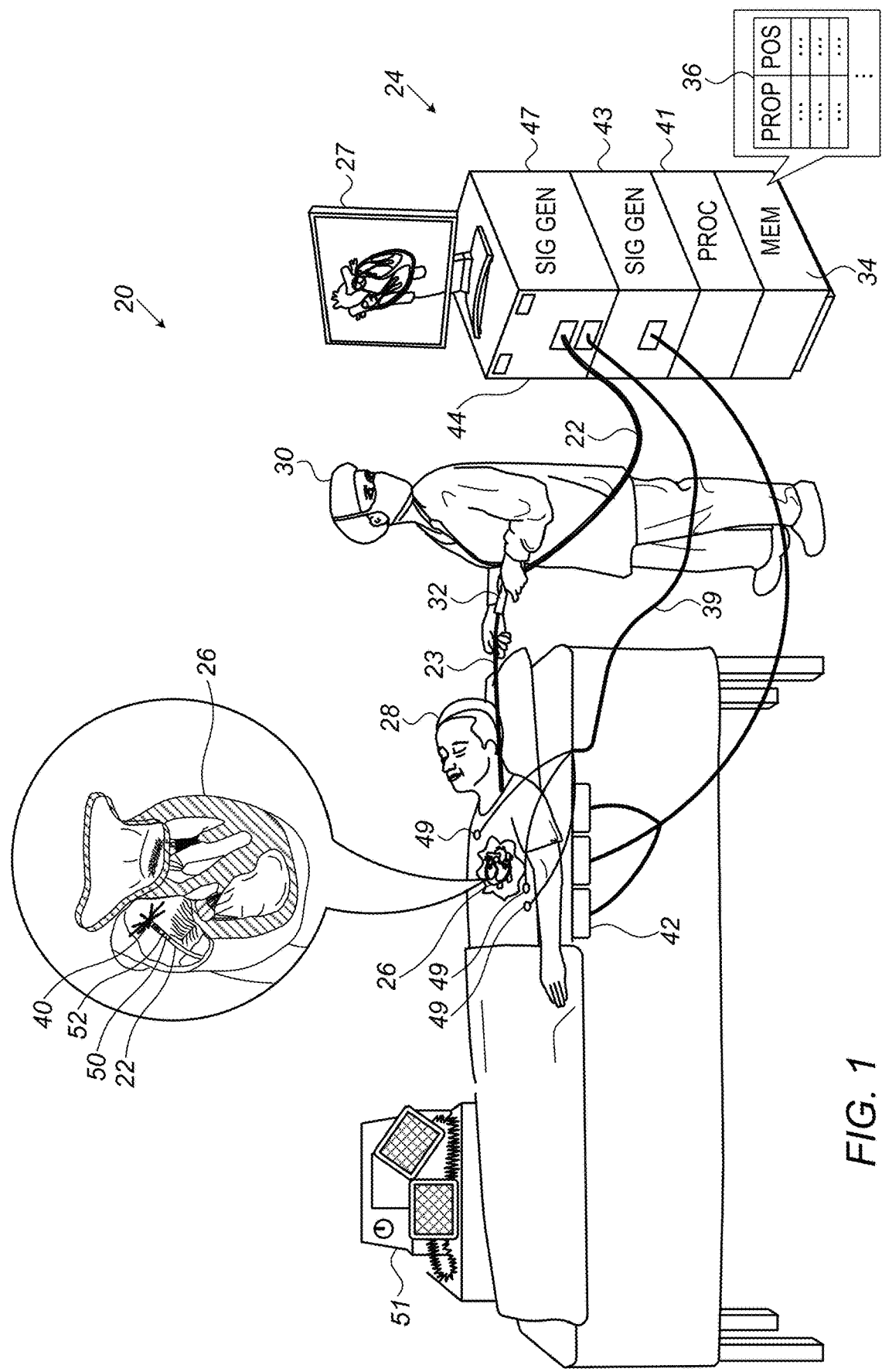
FIG. 1 is a schematic illustration of a system for computing a position map, in accordance with some embodiments of the present invention.
Figure 2A:
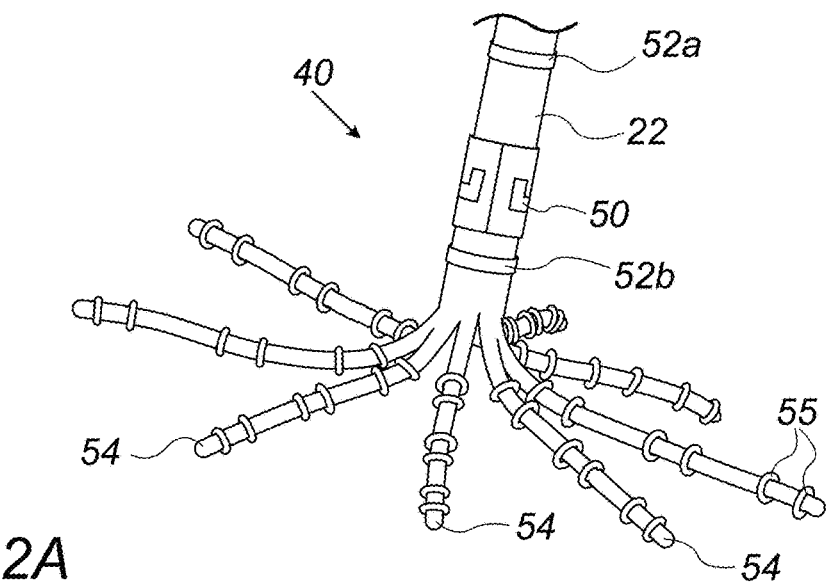
FIGS. 2A-B are schematic illustrations of an intrabody probe, in accordance with some embodiments of the present invention.
Figure 2B:
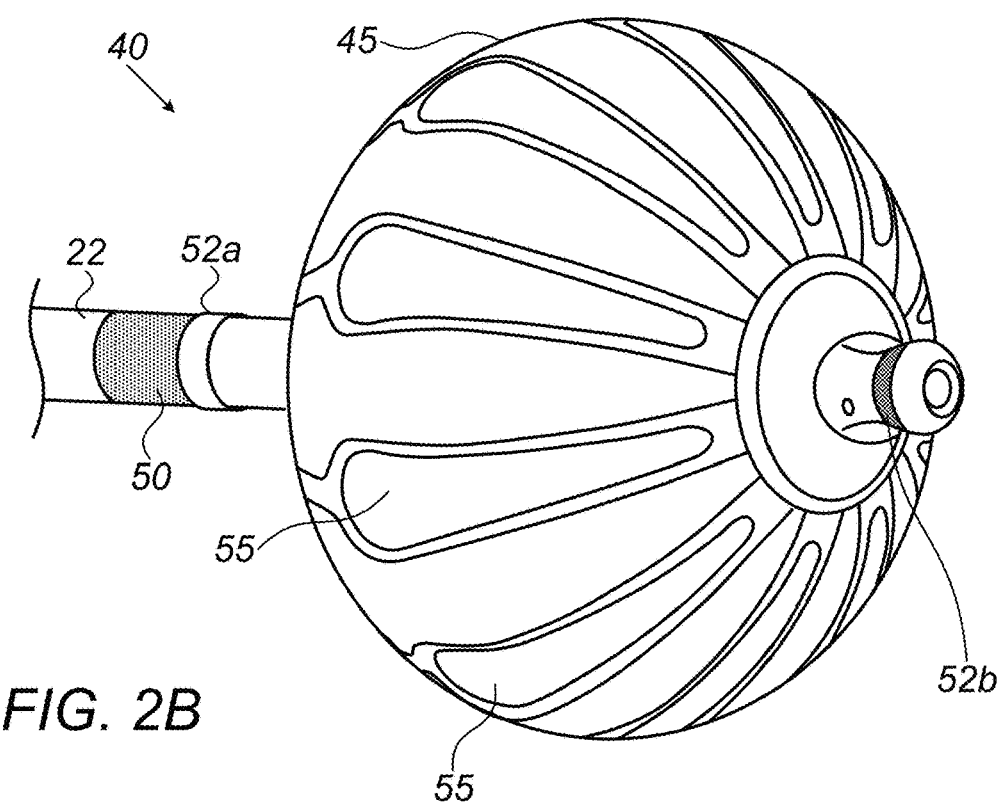

Reference is initially made to FIG. 1, which is a schematic illustration of a system 20 for computing a position map, in accordance with some embodiments of the present invention. Reference is also made to FIGS. 2A-B, which are schematic illustrations of an intrabody probe 40, in accordance with some embodiments of the present invention. Probe 40 comprises a shaft 22, which may be coupled at its distal end to a plurality of deflectable arms 54 (FIG. 2A), an inflatable balloon 45 (FIG. 2B), or any other suitable structure.

Probe 40 comprises one or more position-tracking electrodes 52. For example, as shown in FIGS. 2A-B, the probe may comprise a proximal position-tracking electrode 52a and a distal position-tracking electrode 52b. Probe 40 further comprises an electromagnetic sensor 50, which may be coupled to shaft 22 between the two tracking electrodes (FIG. 2A), proximally to proximal position-tracking electrode 52a (FIG. 2B), or at any other suitable location. Optionally, the probe may further comprise additional electrodes 55 for ablation of cardiac tissue and/or sensing of electrogram signals from the tissue. The aforementioned sensor and electrodes are connected, via wires running through shaft 22, to interface circuitry 44 in a console 24. Interface circuitry 44 may comprise an analog-to-digital (A/D) converter and/or any other suitable components.

As shown in FIG. 1, a physician 30 inserts probe 40 into the vasculature of a subject 28, and then navigates the probe to a target location in a heart 26 of subject 28, typically using a control handle 32 to manipulate shaft 22. Typically, the probe is navigated through a sheath 23, which constrains the distal end of the probe. Subsequently to reaching the target location, sheath 23 is retracted and the distal end of the probe is expanded.

As further shown in FIG. 1, subject 28 is positioned within a magnetic field generated by magnetic-field-generator coils 42. In particular, a first signal generator (SIG GEN) 43 drives a signal through coils 42, such that the coils generate the magnetic field. The magnetic field induces signals in electromagnetic sensor 50, the induced signals varying with the position of the sensor. The induced signals from sensor 50 are received by interface circuitry 44.

In addition, as the probe is moved within heart 26, a second signal generator 47 passes position-tracking signals between position-tracking electrodes 52 and reference electrodes 49. Reference electrodes 49 are located at respective reference positions that do not move with the probe. For example, the reference electrodes may be coupled to the body surface of the subject, such as to the chest and/or back of the subject. In particular, three reference electrodes may be coupled to the chest of the subject (as shown in FIG. 1), and another three reference electrodes may be coupled to the back of the subject. (The reference electrodes are typically connected to interface circuitry 44 via a cable 39.) As the probe is moved, the impedance between position-tracking electrodes 52 and reference electrodes 49 changes, such that the properties of the position-tracking signals vary with the position of the probe.

System 20 further comprises a processor (PROC) 41, which is typically contained in console 24. Processor 41 is configured to control various other components of system 20, such as first signal generator 43 and second signal generator 47. Processor 41 is further configured to receive, via interface circuitry 44, the induced signal from electromagnetic sensor 50. Based on the induced signal, the processor computes the position of probe 40. (The position of the probe may be defined as the position of the sensor, or as the position of another portion of probe 40 at a fixed displacement from the sensor.) In performing this computation, the processor may use any suitable techniques, such as those described in U.S. Pat. Nos. 5,391,199, 5,443,489, and 6,788,967 to Ben-Haim, in U.S. Pat. No. 6,690,963 to Ben-Haim et al., in U.S. Pat. No. 5,558,091 to Acker et al., and in U.S. Pat. No. 6,177,792 to Govari, whose respective disclosures are incorporated herein by reference.

Processor 41 is further configured to receive the position-tracking signals via the interface circuitry, and to ascertain respective sets of properties of the position-tracking signals.

Each set of properties may include, for example, a voltage and/or current between each pair of electrodes, e.g., between proximal position-tracking electrode 52a and each of the reference electrodes and between distal position-tracking electrode 52b and each of the reference electrodes. (In particular, for embodiments in which second signal generator 47 acts as a voltage source, each set of properties may include the current, while for embodiments in which the second signal generator acts as a current source, each set of properties may include the voltage.) Alternatively or additionally, each set of properties may include a calculated impedance between each pair of electrodes.

(It is noted that each of the aforementioned voltages, currents, and impedances may be expressed as an absolute number or as a relative number. As an example of the latter, the current between proximal position-tracking electrode 52a and one of the reference electrodes may be expressed as a proportion of the total current between proximal position-tracking electrode 52a and the reference electrodes.)

Processor 41 is further configured to receive, via the interface circuitry, electrocardiographic potentials from electrocardiogram (ECG) electrodes (not shown) coupled to the subject's body. (The ECG electrodes may be connected to the interface circuitry via cable 39 or another cable.) Using techniques known in the art, the processor combines the potentials into a single electrocardiographic signal.

As further described below with reference to FIG. 3, the processor is configured to build a position map 36, which maps various sets of properties (PROP) to respective positions (POS) of the probe. While map 36 is built, the map may be stored in a memory 34, such as a random access memory (RAM). The process of building position map 36 may be referred to as a "calibration" of the electrode-based tracking system comprising position-tracking electrodes 52 and reference electrodes 49, in that the processor learns the manner in which the properties of the position-tracking signals indicates the position of the probe. Subsequently to calibrating the electrode-based tracking system, the electrode-based tracking system may be used to track another probe, which comprises position-tracking electrodes 52 but not sensor 50, during a subsequent procedure.

While the calibration is performed, probe 40 may be used to ablate intracardiac tissue, construct an electrophysiological map of the target location, and/or perform any other suitable procedure. Alternatively, the calibration may be performed without the simultaneous performance of any other procedure; in such embodiments, the probe need not necessarily comprise any electrodes distally to shaft 22.

Typically, system 20 further comprises a display 27. Based on the computed position of the probe, processor 41 may display, on display 27, an icon representing the probe superimposed over an image of the target location.

In some embodiments, electrodes 55 are used for position tracking, i.e., position-tracking signals are passed between electrodes 55 and reference electrodes 49, and the processor ascertains properties of these signals and builds position map 36 in response thereto. In such embodiments, probe 40 need not necessarily comprise position-tracking electrodes 52.

While the calibration is performed, the subject may require the performance of a cardioversion procedure using a cardioverter 51. As described in detail below with reference to FIG. 3, processor 41 is configured to identify any instance of cardioversion and to pause the calibration in response thereto.

In general, processor 41 may be embodied as a single processor, or as a cooperatively networked or clustered set of processors. The functionality of processor 41 may be implemented solely in hardware, e.g., using one or more fixed-function or general-purpose integrated circuits, Application-Specific Integrated Circuits (ASICs), and/or Field-Programmable Gate Arrays (FPGAs). Alternatively, this functionality may be implemented at least partly in software. For example, processor 41 may be embodied as a programmed processor comprising, for example, a central processing unit (CPU) and/or a Graphics Processing Unit (GPU). Program code, including software programs, and/or data may be loaded for execution and processing by the CPU and/or GPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Identifying Instances of Cardioversion

Figure 3:
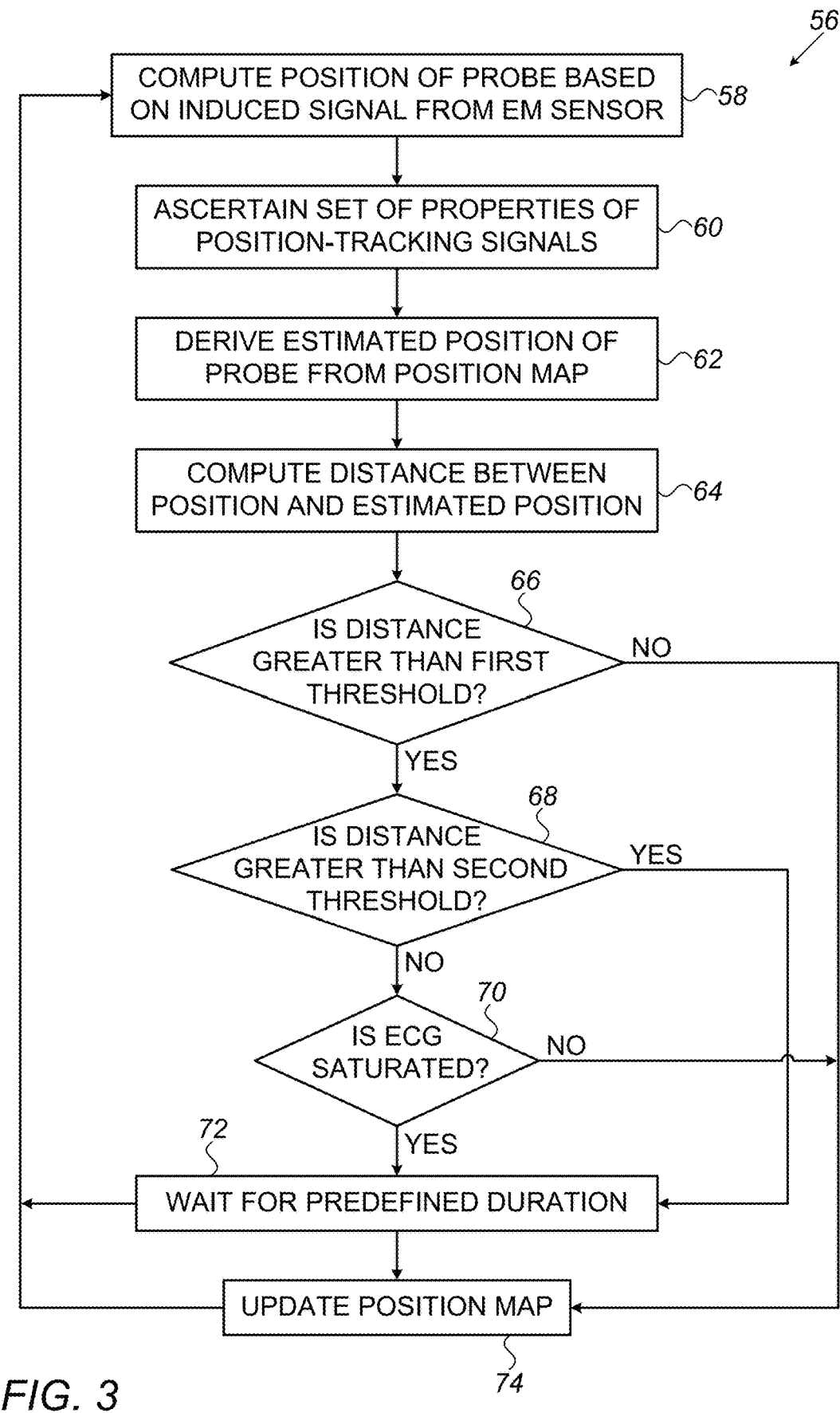
FIG. 3 is a flow diagram for an algorithm for identifying instances of cardioversion while building a position map, in accordance with some embodiments of the present invention.

Reference is now made to FIG. 3, which is a flow diagram for an algorithm 56 for identifying instances of cardioversion while building position map 36, in accordance with some embodiments of the present invention. Algorithm 56 is executed by processor 41, typically in real time, while the probe is inside the subject's heart.

Per algorithm 56, the processor iteratively computes, at a position-computing step 58, the position of the probe within the heart of the subject, based on the induced signal received from the electromagnetic (EM) sensor. For each computation of the probe position, the processor also ascertains the set of properties of the position-tracking signals, at a property-set-ascertaining step 60. Based on the set of properties, the processor derives an estimated position of the probe from position map 36 (FIG. 1), at an estimated-position-deriving step 62.

(It is noted that, during each iteration of algorithm 56, property-set-ascertaining step 60 and, optionally, estimated-position-deriving step 62 may be performed prior to position-computing step 58.)

Subsequently to computing the position of the probe and deriving the estimated position, the processor, at a distance-computing step 64, computes the distance between the position and the estimated position. Next, at a first comparison step 66, the processor compares the distance to a first predefined threshold, which is typically between 8 and 15 mm.

If the distance is not greater than the first threshold, the processor, at a map-updating step 74, updates the position map so as to map the ascertained set of properties to the position. Otherwise, the processor ascertains whether the electrocardiographic signal from the subject is saturated, i.e., whether the amplitude of the electrocardiographic signal exceeds a predefined threshold, at a saturation-checking step 70. If the electrocardiographic signal is not saturated, the processor updates the position map; otherwise, the processor refrains from updating the position map, given that the saturation of the electrocardiographic signal is indicative of cardioversion and hence, reduced reliability of the position-tracking signals.

Subsequently to updating the position map, the processor returns to position-computing step 58.

Typically, if the distance is greater than the first threshold, an update of the position map requires that two conditions be satisfied: first, that the electrocardiographic signal not be saturated (as described above), and second, that the distance not exceed a second predefined threshold, which is typically greater than 15 mm, e.g., between 15 and 30 mm.

For example, prior to performing saturation-checking step 70, the processor may compare the distance to the second predefined threshold at a second comparison step 68. If the distance does not exceed the second predefined threshold, the processor performs saturation-checking step 70. Otherwise, the processor refrains from updating the position map.

In some embodiments, the processor, in response to the electrocardiographic signal being saturated (or in response to the distance being greater than the second threshold), refrains from updating the position map for a predefined duration. In other words, subsequently to ascertaining that the electrocardiographic signal is saturated (or that the distance exceeds the second threshold), the processor waits for the predefined duration, at a waiting step 72. Typically, the predefined duration is between 4 and 5 s, which is generally sufficient time for the electrode-based tracking system to recover from the cardioversion event. Subsequently to waiting, the processor returns to position-computing step 58.

In other embodiments, the processor may update the position map at any subsequent time, provided the conditions for updating the position map are satisfied. In such embodiments, subsequently to ascertaining that the electrocardiographic signal is saturated (or that the distance exceeds the second threshold), the processor returns to position-computing step 58 without first waiting for a predefined duration.

In some embodiments, the algorithm is executed offline, based on recordings of the induced signal, the ECG signal, and the position-tracking signals. In such embodiments, the processor may refrain from using any recorded data acquired within the predefined duration of the time at which ECG saturation occurred (or the time that the distance began to exceed the second threshold) for updating the position map.

Experimental Data

Figure 4:
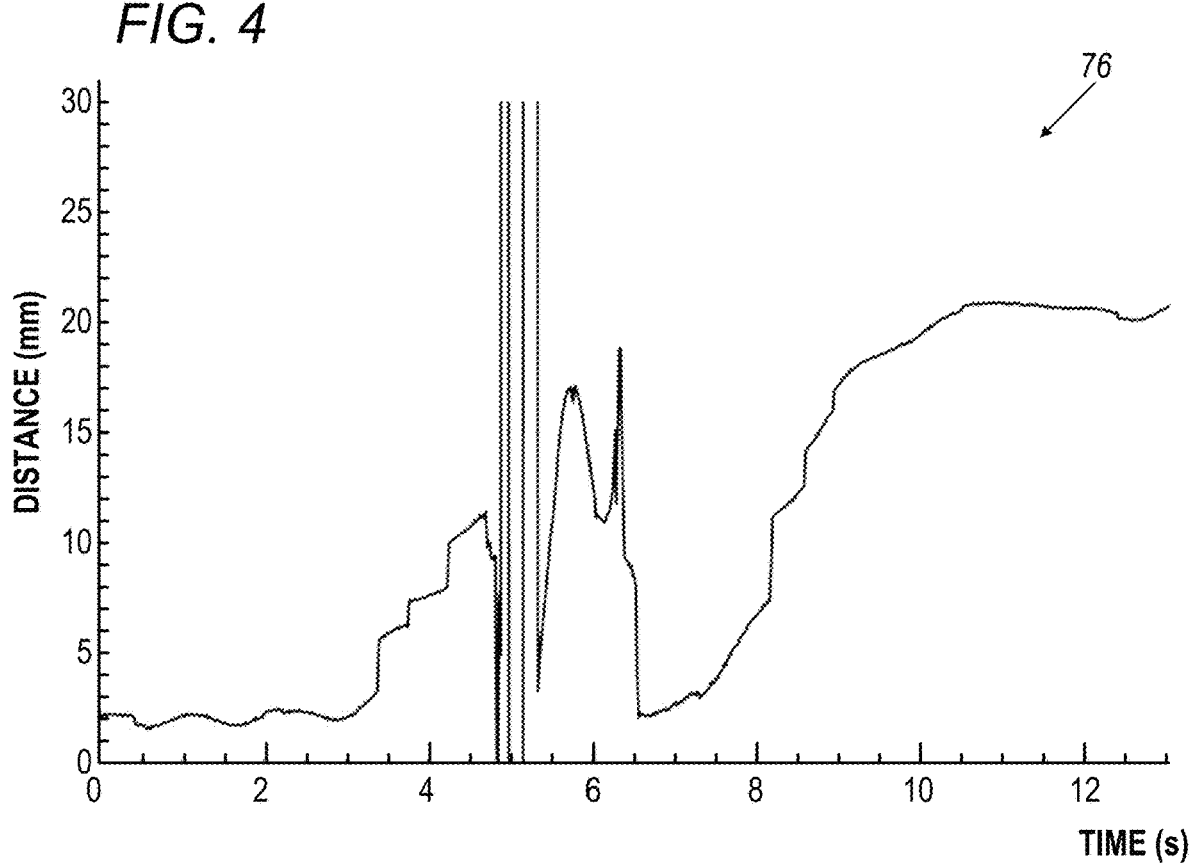
FIG. 4 shows experimental data obtained from a procedure on a human subject performed in accordance with some embodiments of the present invention.
Figure 4:
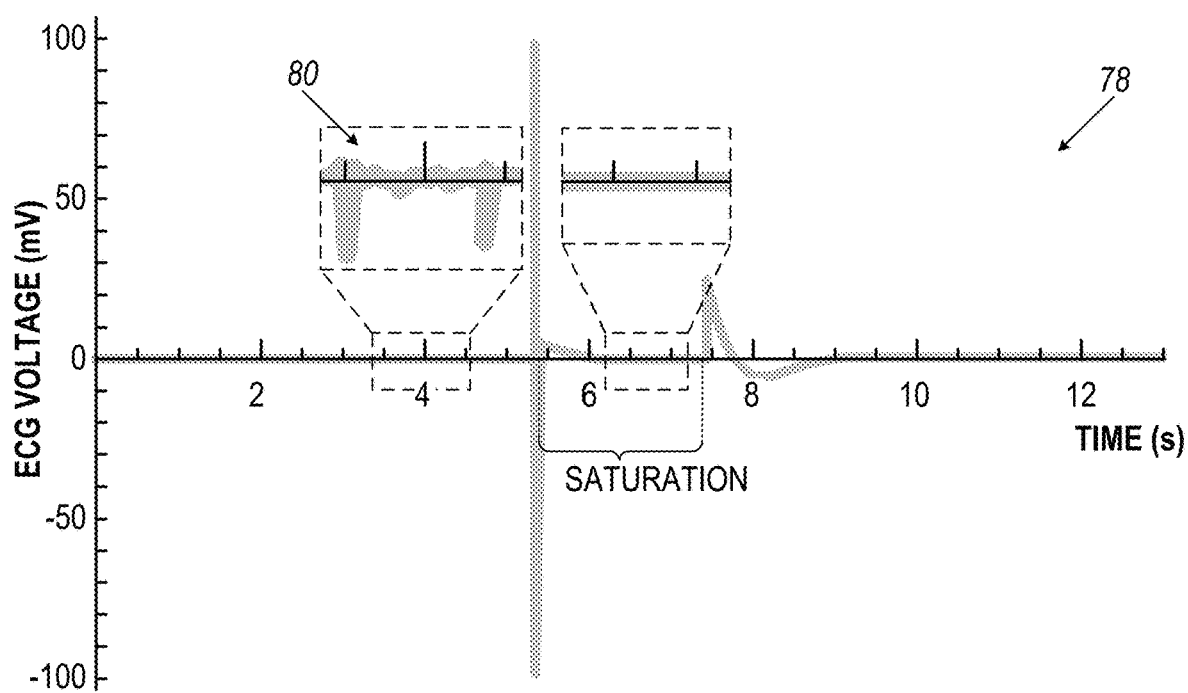

Reference is now made to FIG. 4, which shows experimental data obtained from a procedure performed on a human subject in accordance with some embodiments of the present invention. The data include a first plot 76 of the distance between the position of the probe, as computed based on the induced signal received from the EM sensor, and the estimated position of the probe, as derived from the position map. The data further include a second plot 78 of an ECG signal obtained from the subject during the procedure. The two plots are aligned with respect to the time axis, i.e., the plots are synchronized.

During the procedure, a cardioversion event occurred between approximately 4.525 and 4.528 s. As a result of the cardioversion event, the distance increased substantially from its prior range centered at approximately 2 mm. In addition, the ECG signal became saturated; instead of showing P-Q-R-S-T waves 80, the ECG signal was flat at zero, indicating that the electrocardiographic potential seen at each of the ECG electrodes exceeded the maximum value (100 mV) measurable by system 20, such that the difference between the potentials was zero.

Thus, the experimental data demonstrate that the saturation of the ECG signal is indicative of a cardioversion event. The data further demonstrate that the time for the electrode-based tracking system to recover from the cardioversion event (and hence, for the distance to return to its pre-cardioversion range) may be substantially longer (e.g., 4-5 seconds longer) than the time required for the ECG signal to recover.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
   a memory, configured to store a position map that maps multiple sets of properties to respective estimated positions; and
   a processor, configured to:
      compute a position of an intrabody probe, which includes one or more electrodes and an electromagnetic sensor, within a heart of a subject, based on an induced signal received from the electromagnetic sensor,
      ascertain a set of properties of signals passed between the electrodes and multiple reference electrodes located at respective reference positions,
      based on the set of properties, derive an estimated position of the probe from the position map,
      in response to a distance between the computed position and the estimated position being greater than a predefined threshold, ascertain whether an electrocardiographic signal from the subject is saturated, and
      in response to the electrocardiographic signal not being saturated, update the position map, in the memory, so as to map the set of properties to the computed position,
      wherein the processor is further configured to:
         compute another position of the probe and ascertain another set of properties, and
         in response to the electrocardiographic signal being saturated, refrain from updating the position map so as to map the other set of properties to the other computed position.

2. The system according to claim 1, wherein the predefined threshold is between 8 and 15 mm.

3. The system according to claim 1, wherein the predefined threshold is a first predefined threshold, and wherein the processor is configured to update the position map in response to the distance not exceeding a second predefined threshold.

4. The system according to claim 3, wherein the processor is configured to ascertain whether the electrocardiographic signal from the subject is saturated in response to the distance not exceeding the second predefined threshold.

5. The system according to claim 3, wherein the second predefined threshold is greater than 15 mm.

6. The system according to claim 5, wherein the second predefined threshold is between 15 and 30 mm.

7. The system according to claim 1, wherein the processor is further configured to, in response to the electrocardiographic signal being saturated, refrain from updating the position map for a predefined duration.

8. The system according to claim 7, wherein the predefined duration is between 4 and 5 s.

9. A computer software product comprising a tangible non-transitory computer-readable medium in which program instructions are stored, which instructions, when read by a processor, cause the processor to:
- compute a position of an intrabody probe, which includes one or more electrodes and an electromagnetic sensor, within a heart of a subject, based on an induced signal received from the electromagnetic sensor,
- ascertain a set of properties of signals passed between the electrodes and multiple reference electrodes located at respective reference positions,
- based on the set of properties, derive an estimated position of the probe from a position map that maps multiple sets of properties to respective estimated positions,
- in response to a distance between the computed position and the estimated position being greater than a predefined threshold, ascertain whether an electrocardiographic signal from the subject is saturated, and
- in response to the electrocardiographic signal not being saturated, update the position map so as to map the set of properties to the computed position, wherein the instructions further cause the processor to:
- compute another position of the probe and ascertain another set of properties, and
- in response to the electrocardiographic signal being saturated, refrain from updating the position map so as to map the other set of properties to the other computed position.

* * * * *